United States Patent [19]

Tarrson et al.

[11] Patent Number: 4,691,404
[45] Date of Patent: Sep. 8, 1987

[54] TOOTHBRUSH

[75] Inventors: Emanuel B. Tarrson; Dane Maric, both of Chicago; Thomas P. Kelly, Palatine, all of Ill.

[73] Assignee: John O. Butler Company, Chicago, Ill.

[21] Appl. No.: 856,431

[22] Filed: Apr. 21, 1986

Related U.S. Application Data

[63] Continuation-in-part of Ser. No. 703,745, Feb. 21, 1985, abandoned.

[51] Int. Cl.[4] ............................................... A46B 9/04
[52] U.S. Cl. .................................. 15/167 R; 15/144 R; 15/172; 15/206; 15/184; D4/133
[58] Field of Search ............. 15/143 R, 144 R, 167 R, 15/167 A, 172, 206, 184, 201; 128/62 A; D4/133

[56] References Cited

U.S. PATENT DOCUMENTS

| | | | |
|---|---|---|---|
| D. 157,514 | 2/1950 | Perwas | 15/184 |
| D. 270,669 | 9/1983 | Cassai et al. | D4/133 |
| 759,490 | 5/1904 | Yates | 15/143 R |
| 1,465,522 | 8/1923 | Lundy . | |
| 1,806,520 | 5/1931 | Cave . | |
| 1,894,413 | 1/1933 | Nenning et al. . | |
| 1,996,205 | 4/1935 | Jackson . | |
| 2,164,219 | 6/1939 | McGerry . | |
| 2,167,129 | 7/1939 | Sleeper . | |
| 2,206,542 | 7/1940 | Arnold . | |
| 2,319,841 | 5/1943 | Bate . | |
| 3,204,275 | 9/1965 | Baker . | |
| 3,559,226 | 2/1971 | Burns | 15/167 |
| 3,720,975 | 3/1973 | Nelson | 15/167 R |
| 3,892,040 | 7/1975 | Marquis . | |
| 4,030,199 | 6/1977 | Russell | 15/100 |
| 4,222,143 | 9/1980 | Tarrson et al. | 15/105 |
| 4,387,479 | 1/1983 | Kigyos | 15/167 R |
| 4,520,526 | 6/1985 | Peters | 15/172 X |
| 4,535,761 | 8/1985 | Rabinowitz | 128/62 A |

FOREIGN PATENT DOCUMENTS

| | | | |
|---|---|---|---|
| 519804 | 3/1931 | Fed. Rep. of Germany | 15/206 |
| 671738 | 9/1929 | France | 15/206 |

OTHER PUBLICATIONS

"D-Plak-R", Toothpick Holder, Dental Products Report, 5/74.
A Photograph of three Brushes by Sanyo-Hapics, Perio Pic, from Japan Perio Center, (date unknown).
Page 40 Oral Health, Jan. 1979.
Picture of unknown Japanese Brush (marked Exhibit AS1) of unknown date.
Denticator Brushes, (date unknown).
Photocopy of three Specimens, (marked Exhibit AT2), of unknown date.

*Primary Examiner*—Peter Feldman
*Attorney, Agent, or Firm*—Laff, Whitesel, Conte & Saret

[57] ABSTRACT

An interdental toothbrush has a handle made from a mixture of a thermoplastic elastomer and a general purpose polypropylene. A twisted wire brush projects from the handle in axial alignment therewith. The toothbrush can be held within a loosely clasped fist, with one end of the brush held between a thumb and an index finger. By manipulating the thumb and index finger, the angle at which the brush projects may be changed at will. In this way, the insertion of the brush in more difficult to reach spaces in or around teeth is more easily performed.

21 Claims, 12 Drawing Figures

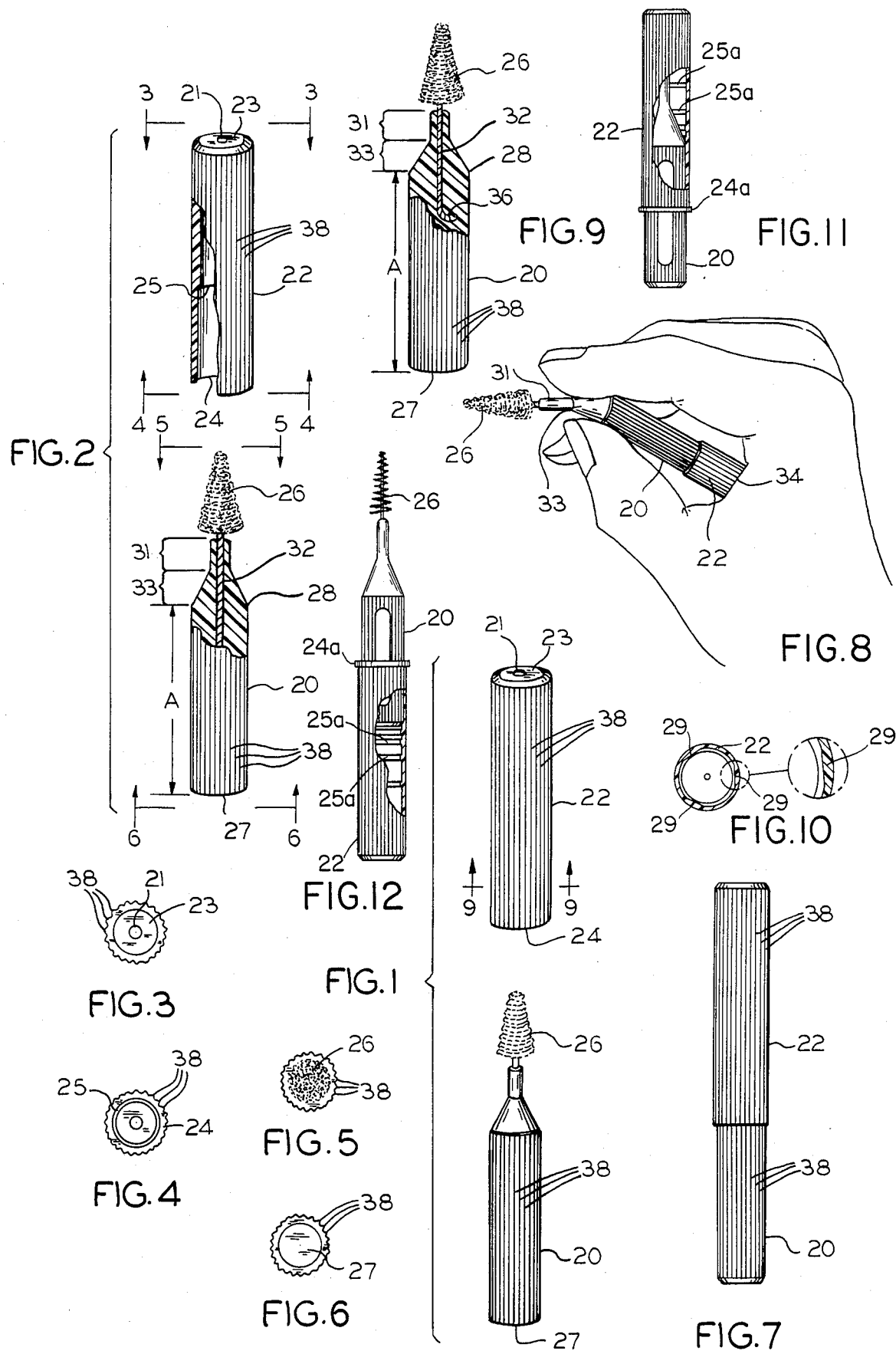

TOOTHBRUSH

This is a continuation-in-part of U.S. Pat. application Ser. No. 06/703,745, filed Feb. 21, 1985, now abandoned.

This invention relates to toothbrushes and, more particularly, to interdental brushes.

An interdental brush is one which fits into spaces between and around the teeth. This kind of brush is generally used by people who have special brushing needs. For example, some bridges are suspensions which run between adjoining teeth. The biting surface is present, but there is nothing under that surface and above the gum line. Therefore, there is a problem of how best to clean under the bridge and against adjacent teeth. Of course, there are many other places where similar interdental brushing problems may occur. Such brushes are shown, for example, in U.S. Pat. Nos. 3,559,226; 4,222,143; 4,387,479, and others.

When traveling or away from home, it is often inconvenient to carry and use long handled interdental brushes of the types shown in the above cited patents. Therefore, small portable devices are available which fit easily into a pocket or purse. These devices often have two parts which include a handle, a brush integral with the handle, and a cover that slips over the brush. Usually, the brush and handle are about two-inches long, with a twisted wire brush projecting out the end of the handle. One such product is marketed by Denticator Company, Inc., of Brisbane, California, under the name "SPIREX V" compact bridge and space brush.

The handle and brush of the prior art devices are generally a rigid unit; therefore, use of the unit is similar to holding a pencil of a comparable length and projecting it into the back of the mouth, while trying to fit the point into a gap under a bridge or between adjacent teeth. This kind of rigidity may require an extension of the cheek or the use of two hands.

Once the gap is found, the brushing must occur without a loss of gap orientation unless one is willing to go through the process of finding the gap again. Also, if one brushes too vigorously and loses the gap while doing so, he may jab himself in the gum or tooth and also bend the wire stem brush. Thus, interdental cleaning may be difficult to perform, especially where visual contact is not easy to achieve.

Accordingly, an object of the invention is to provide new and novel interdental brushes and, more particularly, to provide small and portable units which may be carried in pocket or purse.

Another object of the invention is to provide an interdental brush which may be guided into a brushing position responsive to the user's sense of touch. Yet another object is to provide such a brush which may be guided into position by a slight change in the attitude of the tip of a finger. Here, an object is to provide a brush with a handle which may be flexed at the tip end, especially so that it may be used more easily in the back of the mouth and other hard to reach places in the mouth. In this connection, an object is to provide a brush which is bendable to a proper angle during use and which can be straightened when not in use.

A further object is to provide a brush where very small movements at the tip of the finger may be used to brush in the interdental spaces, thereby reducing the possibility of jabbing the gum responsive to a loss of brush-to-tooth contact.

In keeping with an aspect of the invention, these and other objects are accomplished by providing an interdental brush having a handle with a selected amount of flexibility in a neck region at a junction between the handle and brush, while being substantially rigid in the handle. The dimensions of the brush and handle are such that a small amount of finger pressure upon the neck region causes the tip of the brush to deflect, bend or flex to a convenient brushing angle. After use, the neck may be straightened from the deflected position. The brush may be repeatedly bent and straightened for repeated use. Furthermore, it may be bent at different angles to afford access to different areas of the mouth. Thus, during brushing, one side of the interdental space may be brushed by slightly increasing the deflection responsive to an added finger pressure and the other side of the space may be brushed responsive to decreasing the deflection by reduced finger pressure. If need be, the brush may be rolled between the fingers to enable the finger tip to help straighten or to change the angle of the tip. Thus, the brushing itself may be accomplished by slight movements of the finger tip and thumb.

A preferred embodiment of the invention is shown in the attached drawing in which:

FIG. 1 is a side elevation of the inventive brush and cap, as it might be viewed by the user;

FIG. 2 is a side elevation, partly in cross section, showing the inventive brush and cap;

FIGS. 3—6 are end views taken along lines 3—3 to 6—6, respectively, of FIG. 2;

FIG. 7 is an assembled showing of the cap and brush, as they appear while the brush is being carried in packet or purse, for example;

FIG. 8 shows the brush in operation, illustrating how the brush is deflected responsive to finger pressure;

FIG. 9 shows an alternative embodiment of the invention shown in FIGS. 1-7;

FIG. 10 shows a cross section taken along line 9—9 of FIG. 1;

FIG. 11 is a side elevation of an embodiment of the invention, with the top partially broken away to show internal grooves within the cap, with the cap closed over the handle; and FIG. 12 is a side elevation also showing the embodiment of FIG. 11, with the cap on the bottom of the handle, extending the length thereof.

The brush of FIGS. 1 and 8 include a handle 20 and a cap 22. The cap 22 is a cylindrical member, having one end 23 closed. The other end 24 is open and slips over the brush handle 20 with friction fit (as best seen in FIG. 7). Optionally, one or more vents 21 may be provided in the cap to facilitate drying of the brush after use. A reduction in internal diameter, such as annular stop 25, limits the distance which the cap 22 may be slipped over the end of handle 20 and, therefore, protects the brush 26 from the cap being jammed downwardly.

Internal ribs 29 (FIG. 10) run longitudinally within the cap 22 to provide added friction for holding the cap in place on the handle 20. The added holding forces are required because it is impossible to mold plastic with a completely circular interior to close enough tolerances to always fit snugly. With the longitudinal ribs, the cover will stretch slightly between the ribs on undersize tolerances and yet the unstretched cap still holds on oversize tolerances. The added holding force provided by ribs 29 is especially important if it is necessary to cover the brush after use and while it is still wet. Without the inventive longitudinal ribs, the reduction in friction provided by water, as a lubricant, could create a tendency for the cap to slip off the handle.

In the embodiment of FIG. 2, the internal diameter of the cap is uniform throughout the distance from the step 24 to the closed end 23, to give a smooth internal wall.

It is desirable for the outside of the handle 20 and cap 22 to be serrated, e.g., with longitudinal ribs 38 for aesthetic purposes and so that the toothbrush may be better manipulated by a person with wet hands. These ribs add friction, in the mold, between the cap 22 and the walls of the female cavity in which it was formed. Therefore, when the male member of the mold parts is opened, it sometimes slipped out of the cap 22 of FIG. 2 with the smooth internal wall, leaving the cap 22 trapped inside the female member of the mold. Thus, a knock-out pin would normally be required to be sure that the cap is removed from the mold. Such a knock-out pin may leave an unsightly mark on the cap.

To avoid this problem, the male mold part is given a plurality of circumferential grooves to form a number of circumferential ribs 25a, inside the cap 22. When the male part of the mold is opened, these ribs and grooves are engaged to provide enough holding forces to overcome the friction between the cap 22 and the female mold part. Thereafter, the cap 22 may be knocked off the male part since the depth of the grooves (or the height of the ribs 25a) is relatively small. To help this knock off, without causing a blemish on the cap, a smoothly surfaced flange 24a is formed on the bottom of the cap. This flange also provides a controlled amount of resistance to a flaring of the open end of cap 22 (i.e., it acts somewhat as a rubber band would act to hold the cap 22 in place).

Handle 20 has a twisted wire brush 26 of any suitable design projecting longitudinally therefrom. The opposite end 27 of handle 20 is solid. When the cap 22 is in place on the handle 20, the brush 26 is kept clean and sanitary. When the cap 22 is placed on the opposite end of the handle 20, the handle is made longer.

The internal ribs 29 help secure the cap 22 on the opposite end of the handle 20 so that, together, they provide a more secure tool which may be gripped with greater ease. The added length provided by cap 22 on the end of the handle (FIG. 12) aids the brush in being held within the hand and braced against the palm, as at the fleshy fold 34 (FIG. 8) between the thumb and index finger. The stop 25 limits the distance that the end of the handle 20 extends into the cap 22.

The handle 20 is a solid member which is approximately a quarter-inch in diameter, for a distance A, which may be about one-inch. Beginning at shoulder 28, the diameter of a tip end 30 gradually reduces over a distance, which may be about one-quarter inch, to an outer tip 31, which is also approximately one-quarter inch in length and an eighth-inch in diameter. The wire stem 32 is exposed over a distance between the top of tip end 31 and the bottom of brush 26 which is about one-sixteenth of one-inch.

The wire stem 32 of bursh 26 extends through and is embedded in the tip end and handle of the molded part. This wire stem continues for a substantial distance into the full diameter section of handle 20, as shown, for example in FIG. 2. Preferably, the brush stem 32 is molded into the plastic of the handle at the time when the handle is made. To aid in preventing the brush from being pulled out of the handle, the end of the wire may be bent or crimped, as shown at 36 in FIG. 9.

Longitudinal ribs 38 are provided in the handle 20 and the cap 22. These ribs enhance the esthetic appearance of the product and give the handle and cap a better feel to the user. The ribs also aid in removal of the cap from the handle, particularly after the brush has been used.

In order to achieve a desired flexing characteristic, the handle 20 is preferably made from a mixture of a thermoplastic elastomer, polymer material and a polypropylene of a general purpose homopolymer grade. More particularly, in one embodiment which was constructed and found satisfactory, the handle was made of approximately 80% "C-Flex" and 20% "Polypropylene #5820".

The "C-Flex" material is manufactured by Concept Polymer Technologies, Inc. of 12707 U.S. 19 South, Clearwater, Florida 33546. In its technical data sheets, the manufacturer reports that "C-Flex" has the following properties:

| | ASTM METH-OD | C-FLEX 42-3500 | C-FLEX 42-3510 | C-FLEX 42-3515 |
|---|---|---|---|---|
| MECHANICAL PROPERTIES | | | | |
| Durometer Hardness | D-2240 | 50A | 65A | 70A |
| Tensile Str. Break PSI @ 23° C. | D-412 | 1650 | 1780 | 1900 |
| Tensile Modulus | | | | |
| PSI at 100% | D-412 | 175 | 330 | 340 |
| PSI at 300% | D-412 | 310 | 540 | 650 |
| Tensile - Set % (5) after Break | D-412 | 55 | 100 | 43 |
| Elongation % at Break @ 23° C. | D-412 | 850 | 800 | 790 |
| Compression Set at 70° C. | D-395 | 72 | 66 | 70 |
| Tear Strength - Method-Die C lbs/in | D-624 | 130 | 183 | 220 |
| Specific Gravity ± .02 | D-792 | .90 | .90 | .90 |
| Water Absorption (5) at 73° F. | | | | |
| 1 week at 50% RH | D-570 | .14 | .27 | .30 |
| 1 week at 100% RH | D-570 | .42 | .26 | .17 |
| THERMAL PROPERTIES | | | | |
| Brittle Temperature | D-746 | −100° F. | −100° F. | −100° F. |
| Melt Index-Cond. E | D-1238 | .25 | 1.9 | 1.8 |
| ELECTRICAL PROPERTIES | | | | |
| Dielectric Strength (Volts/Mil) | | 450 | 740 | 800 |
| Volume Resistivity ($10^{16}$ ohm-cm) | | 1.2 | 3.0 | 0.8 |
| Surface Resistivity ($10^{15}$ ohm) | | 3.6 | 3.6 | 2.6 |
| Dielectric Constant | | | | |
| ($10^2$ Hz) | | 2.33 | 2.27 | 2.27 |
| ($10^3$ Hz) | | 2.33 | 2.27 | 2.27 |
| ($10^6$ Hz) | | 2.31 | 2.27 | 2.15 |
| Dissipation Factor | | | | |
| ($10^2$ Hz) | | 0.0004 | 0.0002 | 0.0002 |
| ($10^3$ Hz) | | 0.0006 | 0.0002 | 0.0002 |
| ($10^6$ Hz) | | 0.0022 | 0.0008 | 0.0008 |

Polypropylene #5820 (12 melt) is manufactured by the Shell Chemical Company, having an address at 1415 West 22 Street, Oak Brook, Illinois 60521. The manufacturer of this product describes its physical properties as follows:

| TRADITIONAL PROPERTY | SI UNITS | ASTM UNITS | TEST |
| --- | --- | --- | --- |
| Melt Flow | 12 g/10 min | 12 g/10 min | D 1238[1] |
| Density at 23° C. | 0.903 g/cc | 0.903 g/cc | D 1505 |
| Tensile yield strength, at 2.0 in/min | 5100 psi | 35 MPa | D 638[2] |
| Yield elongation at 2.0 in/min | 10% | 10% | D 638[2] |
| 1% Secant modulus, at 0.2 in/min | 200,000 psi | 1375 MPa | D 638[2] |
| Flexural modulus, at 0.05 in/min, in span | 220,000 psi | 1500 MPa | D 790A[2] |
| Notched Izod impact strength, | | | |
| at 73° F./23° C. | 0.5 ft-lb/in | 27 J/m | D 256[2] |
| at 0° F./−18° C. | 0.4 ft-lb/in | 20 J/m | D 256[2] |
| Hardness, Rockwell | R95 | R95 | D 785 |
| Heat deflection temp at 66 psi/455 kPa | 220° F. | 104° C. | D 648 |
| Vicat softening temp | 305° F. | 152° C. | D 1525 |

[1]Condition L, 230° C., 2160 g
[2]ASTM Type 1 specimen, ⅛" thick (injection molded)

Shell further describes this product as being a high flow, general purpose material suitable for injection molding of intricate parts where long flow paths are involved. An antistat component reduces electrical charges during processing and subsequent storage, thereby reducing dust pickup. The manufacturer claims that the product has an excellent flex life, good chemical and solvent resistance, high strength-to-weight ratio, and exceptional stress cracking resistance.

Both of these materials meet exacting Federal standards for bio-medical use and for making direct contact with food.

To further control the amount of flexing which may occur in the neck region 30, 31, the diameter of wire stem 32 may be either increased or decreased somewhat and the diameter and length of the neck region 30, 31 may be modified. It is thought that those who manufacture the inventive brush will determine the best diameters and lengths for themselves and for their own particular needs. In general, the wire stem of a conventional interdental brush may be increased in diameter in the approximate range of 10–50%.

The method of using the inventive brush is shown in FIG. 8. The length of handle 20 is such that, when the tip end 30 is held between the thumb and index finger, the opposite end of the handle is captured and stabilized along the length of the finger. Or, if the cap is in place on the end of the brush, its end might be captured in or near the palm of the hand, as in the fleshy fold 34, which is between the thumb and index finger. By pressing the index finger against the tip end 30 while holding the handle 20 by the thumb, it is possible to deflect, bend, or flex, the brush to point, more or less, in line with the finger tip. If the user wishes to point the brush in another direction, the handle may be rolled between the thumb and index finger or a small amount of thumb pressure may be applied to the brush to straighten it or bend it to the other position. Thus, the flexed angle of the brush may be varied, at the will of the user.

It is relatively easy to point one's finger at an object since the sense of touch tends to assist the pointer. This makes the invention easy to use. On the other hand, it is more difficult to point an instrument with a relatively long handle since the instrument may be held at almost any angle and since the user cannot always take advantage of the sense of touch to tell the user where the tip end of the long handled brush is located. Moreover, none of the existing long-handled or other interdental brushes have flexible tip ends similar to the inventive brush so their tip ends cannot be deflected as in the inventive brush. While the tip end is held and deflected, as seen in FIG. 8, use of the instrument is much more like pointing a finger since the method of bending inherently tends to align the brush with the finger. This is an important advantage over the prior interdental brushes.

Another factor is that, when the brush is held in the hand as seen in FIG. 8, it is much easier to place the brush in the space between the teeth in the back of the mouth as compared to attempting to position it when the brush is straight, as seen in FIG. 1, because the natural curvature of the hand in this position is most appropriate to reaching into that back of the mouth space. An advantage is that the portion of the wire brush encased in plastic is more resistant to breaking from repeated or excessive bending than would be the case if the wire were exposed.

Those who are skilled in the art will readily perceive how to modify the invention. Therefore, the appended claims are to be construed to cover all equivalent structures which fall within the true scope and spirit of the invention.

The claimed invention is:

1. An interdental toothbrush comprising a plastic handle having a first portion of reduced cross section at one end with a flexing and substantially resilient capability which may be controlled by being held between a thumb and index finger, and a second portion of a larger cross-section which is relatively rigid and of a length which enables the opposite end of the handle to be captured and stabilized in the hand, brushing means having a brush with a twisted wire stem embedded in at least said first portion of the handle and projecting from said first portion in axial alignment with the handle, said controlled flexing and resiliency of said first portion of the handle being such that when said first portion is held between said thumb and index finger a small amount of thumb and finger pressure flexes said first portion of the handle to project said brush from said handle at an angle responsive to a manipulation of the thumb and index finger which enables said brush to be inserted into hard to reach places around and between the teeth.

2. The toothbrush of claim 1 wherein the length is such that said second portion of said toothbrush handle is captured along the length of the finger when said first portion is held by the thumb and index finger.

3. The toothbrush of claim 1 wherein the length is such that said second portion of said toothbrush handle is captured in approximately the palm of the hand when said first portion is held by the thumb and index finger.

4. The toothbrush of claim 2 wherein said first portion is approximately one-half inch long and tapers for approximately one-quarter inch diameter near said second portion to about one-eighth inch diameter, and said first portion has a tip at the outer end which is about one-eighth inch in diameter and approximately one-quarter inch long.

5. The toothbrush of claim 4 wherein said twisted wire brush has a diameter which is selected to provide said controlled flexibility.

6. The toothbrush of claim 5 and cap means for covering said first portion and said twisted wire brush.

7. The toothbrush of claim 6 wherein said cap means are adapted to receive the second portion of the handle when the cap is removed from the first portion and means are provided in said cap means for limiting movement of first and second portions when they are inserted in the cap.

8. The toothbrush of claim 7 wherein the second portion of the handle and the cap are provided with longitudinal ribs extending along a major portion of their lengths.

9. The brush of claim 1 wherein said handle is made from a composition of a thermoplastic elastomer polymer and a general purpose polypropylene.

10. The brush of claim 9 wherein said composition is approximately 80% of said thermoplastic elastomer and 20% of said polypropylene.

11. A toothbrush comprising a twisted wire brush having a stem embedded in a plastic handle and a cap for covering said brush, said handle having a flexibility and substantial resiliency in at least part of an area at one end of said handle where said stem is embedded, said one end of the handle being of reduced cross-section with respect to the remainder of said handle, the flexibility and resiliency being such that a manipulation of a tip end of said handle in the vicinity of said area flexes said tip end and said twisted wire brush to point said brush a selected angle, with respect to the axis of said handle.

12. The brush of claim 11 wherein said angle may be changed repeatedly by continuously manipulating said tip end.

13. A toothbrush having a handle made from a mixture of approximately 80% thermoplastic elastomer and 20% general purpose polypropylene, a twisted wire brush having a stem embedded in said handle and projecting from the handle in axial alignment therewith, the brush having dimensions which can be held within a loosely clasped fist, with one end of the brush held captured between a thumb and an index finger and the other end of the brush captured along the length of the index finger, the part held by the thumb and index finger being reduced in cross-section with respect to the remainder of the handle and having a flexibility and a resiliency such that by manipulating the thumb and index finger, the angle at which the brush projects from the hand may be changed at will.

14. The toothbrush of claim 13, wherein a cap is provided which fits over the twisted wire brush when the brush is not in use and which may be removed from the brush end of the handle and attached to the opposite end of the handle to extend the length of the toothbrush when the toothbrush is in use.

15. The toothbrush of claim 6 wherein said cap means includes at least one internal longitudinal rib for adding friction to secure it when in place over said handle, said cap being resilient to be somewhat stretched responsive to a bulk of material provided by said internal longitudinal rib when said cap is slipped over said handle.

16. The toothbrush of claim 15 wherein there are three of said internal longitudinal ribs distrubuted equally around the inside periphery of the cap.

17. The toothbrush of claim 7 wherein said cap means includes at least one internal longitudinal rib for adding friction to secure it when in place over said handle, said cap being resilient to be somewhat stretched responsive to a bulk of material provided by said internal longitudinal rib when said cap is slipped over said handle.

18. The toothbrush of claim 14 wherein said cap means includes at least one internal longitudinal rib for adding friction to secure it when in place over said handle, said cap being resilient to be somewhat stretched responsive to a bulk of material provided by said internal longitudinal rib when said cap is slipped over said handle.

19. The toothbrush of claim 6 wherein said cap means is a molded plastic item, said cap including at least one internal circumferential rib, said rib having a height which is great enough to cling to one mold part when a mold is opened, thereby pulling the cap from another mold part, and said rib height being small enough for said cap to be knocked off said one mold part after said mold is opened.

20. The toothbrush of claim 12 wherein said cap means is a molded plastic item made in a mold with at least two parts, said cap including at least one internal circumferential rib, said rib having a height which is great enough to cling to one mold part when a mold is opened, thereby pulling the cap from another mold part, and said rib height being small enough for said cap to be knocked off said one mold after said mold part is opened.

21. The toothbrush of claim 20 and a flange on an end of said cap for receiving a tool for removing said cap from said one mold part and for providing an elastic band for holding said cap in place.

* * * * *